United States Patent [19]

Talanian et al.

[11] Patent Number: 5,492,824
[45] Date of Patent: Feb. 20, 1996

[54] ICE AND ICE-LIKE COMPOSITIONS AND METHODS OF MAKING SAME

[75] Inventors: Robert V. Talanian, Needham, Mass.; Leonard L. C. Dang, Hancock, N.H.; Nigel P. C. Walker, Dossenheim, Germany; Tariq Ghayur, Grafton, Mass.

[73] Assignee: BASF AG, Worcester, Mass.

[21] Appl. No.: 242,663

[22] Filed: May 12, 1994

[51] Int. Cl.⁶ .................................................. C12N 9/64
[52] U.S. Cl. ...................... 435/226; 435/184; 435/219; 530/351
[58] Field of Search ..................... 435/226, 184, 435/219; 530/351

[56] References Cited

U.S. PATENT DOCUMENTS 5,278,061  1/1994  Bull et al. ............................... 435/212

OTHER PUBLICATIONS

Thornberry, N. A., et al. (1992) Nature 356, 768–774.
Miller, D. K., et al. (1993) J. Biol. Chem. 268 (24), 18062–18069.
Thornberry, N. A., et al. (1994) Biochemistry 33, 3934–3940.

*Primary Examiner*—Charles L. Patterson, Jr.
*Attorney, Agent, or Firm*—Wolf, Greenfield & Sacks

[57] ABSTRACT

The present invention is directed to ICE and ICE-like compositions formed by combining two subunits of ICE and folding such subunits to form an active enzyme.

46 Claims, 2 Drawing Sheets

FIGURE 1

```
ATG GCC GAC AAG GTC CTG AAG GAG AAG AGA AAG CTG TTT ATC CGT TCC     48
ATG GGT GAA GGT ACA ATA AAT GGC TTA CTG GAT GAA TTA TTA CAG ACA     96
AGG GTG CTG AAC AAG GAA GAG ATG GAG AAA GTA AAA CGT GAA AAT GCT    144
ACA GTT ATG GAT AAG ACC CGA GCT TTG ATT GAC TCC GTT ATT CCG AAA    192
GGG GCA CAG GCA TGC CAA ATT TGC ATC ACA TAC ATT TGT GAA GAA GAC    240
AGT TAC CTG GCA GGG ACG CTG GGA CTC TCA GCA GAT CAA ACA TCT GGA    288
AAT TAC CTT AAT ATG CAA GAC TCT CAA GGA GTA CTT TCT TCC TTT CCA    336
GCT CCA CAG GCA GTG CAG GAC AAC CCG GCT ATG CCG ACC TCT TCT GGT    384
TCT GAA GGT AAC GTT AAA CTG TGC TCT CTG GAA GAA GCT CAA AGG ATA    432
TGG AAA CAA AAG TCG GCA GAG ATT TAT CCA ATA ATG GAC AAG TCA AGC    480
CGC ACA CGT CTT GCT CTC ATT ATC TGC AAT GAA GAA TTT GAC AGT ATT    528
CCT AGA AGA ACT GGA GCT GAG GTT GAC ATC ACA GGC ATG ACA ATG CTG    576
CTA CAA AAT CTG GGG TAC AGC GTA GAT GTG AAA AAA AAT CTC ACT GCT    624
TCG GAC ATG ACT ACA GAG CTG GAG GCA TTT GCA CAC CGC CCA GAG CAC    672
AAG ACC TCT GAC AGC ACG TTC CTG GTG TTC ATG TCT CAT GGT ATT CGG    720
GAA GGC ATT TGT GGG AAG AAA CAC TCT GAG CAA GTC CCA GAT ATA CTA    768
CAA CTC AAT GCA ATC TTT AAC ATG TTG AAT ACC AAG AAC TGC CCA AGT    816
TTG AAG GAC AAA CCG AAG GTG ATC ATC ATC CAG GCC TGC CGT GGT GAC    864
AGC CCT GGT GTG GTG TGG TTT AAA GAT TCA GTA GGA GTT TCT GGA AAC    912
CTA TCT TTA CCA ACT ACA GAA GAG TTT GAG GAT GAT GCT ATC AAA AAA    960
GCT CAC ATC GAA AAA GAC TTC ATC GCT TTC TGC TCT TCC ACA CCA GAT   1008
AAT GTT TCT TGG AGA CAT CCC ACA ATG GGC TCT GTT TTT ATT GGA AGA   1056
CTC ATT GAA CAT ATG CAA GAA TAT GCC TGT TCC TGT GAT GTG GAG GAA   1104
ATT TTC CGC AAG GTT CGA TTT TCA TTT GAG CAG CCA GAT GGT AGA GCG   1152
CAG ATG CCC ACC ACT GAA AGA GTG ACT TTG ACA AGA TGT TTC TAC CTC   1200
TTC CCA GGA CAT TAA                                               1215
```

FIGURE 2

```
Met Ala Asp Lys Val Leu Lys Glu Lys Arg Lys Leu Phe Ile Arg Ser
 1           5                  10                  15
Met Gly Glu Gly Thr Ile Asn Gly Leu Leu Asp Glu Leu Leu Gln Thr
            20                  25                  30
Arg Val Leu Asn Lys Glu Met Glu Lys Val Lys Arg Glu Asn Ala
            35              40              45
Thr Val Met Asp Lys Thr Arg Ala Leu Ile Asp Ser Val Ile Pro Lys
        50              55              60
Gly Ala Gln Ala Cys Gln Ile Cys Ile Thr Tyr Ile Cys Glu Glu Asp
65              70              75                      80
Ser Tyr Leu Ala Gly Thr Leu Gly Leu Ser Ala Asp Gln Thr Ser Gly
                85              90              95
Asn Tyr Leu Asn Met Gln Asp Ser Gln Gly Val Leu Ser Ser Phe Pro
            100             105                 110
Ala Pro Gln Ala Val Gln Asp Asn Pro Ala Met Pro Thr Ser Ser Gly
        115             120             125
Ser Glu Gly Asn Val Lys Leu Cys Ser Leu Glu Glu Ala Gln Arg Ile
    130             135             140
Trp Lys Gln Lys Ser Ala Glu Ile Tyr Pro Ile Met Asp Lys Ser Ser
145             150             155             160
Arg Thr Arg Leu Ala Leu Ile Ile Cys Asn Glu Glu Phe Asp Ser Ile
                165             170             175
Pro Arg Arg Thr Gly Ala Glu Val Asp Ile Thr Gly Met Thr Met Leu
            180             185             190
Leu Gln Asn Leu Gly Tyr Ser Val Asp Val Lys Lys Asn Leu Thr Ala
        195             200             205
Ser Asp Met Thr Thr Glu Leu Glu Ala Phe Ala His Arg Pro Glu His
    210             215             220
Lys Thr Ser Asp Ser Thr Phe Leu Val Phe Met Ser His Gly Ile Arg
225             230             235             240
Glu Gly Ile Cys Gly Lys Lys His Ser Glu Gln Val Pro Asp Ile Leu
            245             250             255
Gln Leu Asn Ala Ile Phe Asn Met Leu Asn Thr Lys Asn Cys Pro Ser
        260             265             270
Leu Lys Asp Lys Pro Lys Val Ile Ile Ile Gln Ala Cys Arg Gly Asp
    275             280             285
Ser Pro Gly Val Val Trp Phe Lys Asp Ser Val Gly Val Ser Gly Asn
    290             295             300
Leu Ser Leu Pro Thr Thr Glu Glu Phe Glu Asp Asp Ala Ile Lys Lys
305             310             315             320
Ala His Ile Glu Lys Asp Phe Ile Ala Phe Cys Ser Ser Thr Pro Asp
            325             330             335
Asn Val Ser Trp Arg His Pro Thr Met Gly Ser Val Phe Ile Gly Arg
            340             345             350
Leu Ile Glu His Met Gln Glu Tyr Ala Cys Ser Cys Asp Val Glu Glu
        355             360             365
Ile Phe Arg Lys Val Arg Phe Ser Phe Glu Gln Pro Asp Gly Arg Ala
    370             375             380
Gln Met Pro Thr Thr Glu Arg Val Thr Leu Thr Arg Cys Phe Tyr Leu
385             390             395             400
Phe Pro Gly His
```

ICE AND ICE-LIKE COMPOSITIONS AND METHODS OF MAKING SAME

FIELD OF THE INVENTION

This invention features interleukin-1 beta converting enzyme (ICE), ICE-like compositions and methods of making such compositions.

BACKGROUND OF THE INVENTION

Interleukin-1 (IL-1) plays an important role in the pathogenesis of several inflammatory disorders. Two proteins displaying IL-1 activity have been described, interleukin-1-alpha (IL-1α) and interleukin-1-beta (IL-1β).

Although the two proteins are products of distinct genes, they share 27–33% amino acid identity, and are known to interact with the same receptor and have similar biological activity. Each protein is proteolytically cleaved from its approximately 31 kDa precursor to its more active 17 kDa form. IL-1α precursor (preIL-1α) displays bioactivity, although less than that of its mature form. In contrast, IL-1β precursor (preIL-1β) displays no biological activity until processed to its mature form. Although both IL-1 molecules are secreted proteins, both lack signal peptides. The mechanism(s) of secretion have not been fully defined.

Only certain cell types process preIL-1β and secrete IL-1β. Monocytes and macrophages are the most efficient and prolific producers and secretors of IL-1β known. Of the two IL-1 proteins synthesized and secreted following activation of monocytes and macrophages, IL-1β is the more abundant.

The cellular processing of preIL-1β to IL-1β is mediated by the enzyme, IL-1β Converting Enzyme (IL-1CE or ICE). ICE is expressed in vivo as a 45 kDa precursor molecule which is proteolytically processed in vivo into fragments of 20 and 10 kDa, that together comprise the active form of ICE.

The study of IL-1β and the role it plays in the pathogenesis of several inflamatory disorders has been hampered by an insufficient amount of ICE. In vivo, monocytes and macrophages contain only small quantities of IL-1β and ICE. Both ICE and IL-1β are present in low quantities in cells, which limits the amount of material available for study and characterization. It has been reported that active ICE could not be produced by mixing the major protein subunits together, after separate expression in *E. coli*, or by coexpressing the subunits in *Escherichia coli*. Miller et al, "Purification and Characterization of Active Human Interleukin-1β-converting Enzyme from THP.1Monocyte Cells", *J. Biol. Chem.* 268, pp 18062–18069 (1993). The present invention directly contradicts the teaching of Miller et al.

Substances that interact with ICE and alter the production of IL-1β are of interest as therapeutics to modulate the inflammatory response.

SUMMARY OF THE INVENTION

The present invention is directed to ICE, ICE-like compositions and methods for making ICE and ICE-like compositions. One embodiment of the present invention features a method of making ICE and ICE-like compositions. The method comprises the steps of combining a first and second subunit of ICE or an ICE-like composition and folding the subunits to form an ICE or ICE-like composition.

As used herein, "ICE" refers to IL-1β converting enzyme as defined in European Patent Application No. 92307479.3 having a filing date of Aug. 14, 1992 by Merck and Company, Inc. The term "ICE-like composition" refers to compositions that have ICE activity, that is, that convert the 31 kDa precursor protein, preIL-1β, into a 17 kDa mature, bioactive IL-1β molecule. By way of example, without limitation, such ICE-like compositions comprise separately expressed, combined and folded 10 and 20 kDa subunits or fragments of ICE, recombinant ICE, subunits or fragments derived from the 45 kDa pre-ICE molecule (including but not limited to a 32 kDa subunit or fragment) and proteins resembling ICE with non-critical amino acid deletions, substitutions and additions.

Separately expressed subunits or fragments, and recombinant ICE further comprise such additional amino acids that are added to mammalian proteins when the nucleic acids encoding such proteins are expressed in bacterial systems, and restriction sites and other features of DNA constructs encoding ICE, which permit cloning or improve expression of ICE. This application uses the terms "subunit" and "fragment" interchangeably to denote derivation from the preICE composition.

As used herein, the term "combined" refers to being brought in proximity to each other as in forming an admixture. The term "folding" refers to the protein subunits or fragments coming together to form a catalytically active composition.

Preferably, the method further comprises the step of expressing a nucleic acid encoding a first subunit of the mature form of ICE or an ICE-like composition and a second subunit of the mature form of ICE or an ICE-like composition. Preferably, the two subunits of ICE or an ICE-like composition are separately expressed. As used herein, "expressed" refers to transcription and translation of nucleic acid to form proteins. The term "separately expressed" means that the protein sequence comprising each subunit is encoded by nucleic acids which upon translation and transcription produces two distinct protein subunits. The nucleic acid coding each protein may be linked together on one nucleic acid molecule or may be carried on two distinct nucleic acid molecules. By way of example, without limitation, the nucleic acid may be contained on a single plasmid, which plasmid has two regions, each region encoding for one of the subunits. Each region of the plasmid may be under the influence of separate promoters. By way of example, without limitation, the nucleic acid coding each subunit may be carried on separate plasmids for incorporation into a single cell. By way of example, without limitation, the first nucleic acid may be contained in one group of cells and the second nucleic acid contained in a second group of cells.

The present method can be utilized with any cell capable of being transformed to make the first and second subunits of ICE or an ICE-like composition. Preferably, the cell which is transformed is *Escherichia coli*. A preferred *E. coli* comprises *E. coli* CAG 597. *E. coli* CAG 597 is described in U.S. Pat. No. 4,758,512 having a filing date of Mar. 6, 1984 by President and Fellows of Harvard College, Cambridge, Mass. *E. coli* CAG 597 is available commercially.

Preferably, the first nucleic acid has a sequence encoded by nucleotides 358 to 891 of Seq. I.D. No. 1. Preferably, the second nucleic acid has nucleotide sequences corresponding to 994 to 1212 nucleotides of Seq. I.D. No. 1, which nucleotides correspond to an 18 kDa subunit, and; most preferably, corresponding to 949 to 1212 nucleotides of Seq.

ID No. 1, which nucleotides correspond to a 20 kDa subunit. Such nucleic acids can be expressed in *E. coli* cells when operably linked to a promoter. As used herein, the term "operably linked" refers to nucleic acid that is associated in a manner that allows transcription and translation by a cell in which it is placed. Typically, the nucleic acid and promoter are incorporated into a vector that is received by the cell. The protein so formed is capable of being folded to form ICE or an ICE-like composition. Bacterial expression systems may require additional amino acids, including a methionine on the first and/or second subunit of ICE. The additional amino acids do not appear to detract from the biological activity of the combined and folded protein.

The protein sequence of pre-ICE is set forth in SEQ. ID No. 2. The 20 kDa subunit spans amino acids 120 to 297. Two 22 kDa subunits which may have activity similar to the 20 kDa subunit comprise amino acids 104 to 297 and amino acids 120 to 316. An 18 kDa subunit which may have activity similar to the 20 kDa subunit spans amino acids 135 to 297. Thus, one embodiment of the present invention features an 18 to 24 kDa subunit selected from amino acids 104 to 316 of Seq. ID No. 2.

The 10 kDa subuit spans amino acids 317 to 404. A 12 kDa subunit which may have activity similar to the 10 kDa subunit spans amino acids 299 to 404. Thus, one embodiment of the present invention features a 10 to 12 kDa subunit selected from amino acids 298 to 404 of Seq. ID No. 2.

Preferably, the first and second subunits are reduced and denatured prior to the step of combining to form an admixture. The first and second subunits are denatured by imposing denaturing conditions. These conditions comprise forming solutions of the first and the second subunits which solutions incorporate chaotropic agents, reducing agents, and elevated pH. Chaotropes are compounds which cause disruption and denaturation of proteins. A preferred chaotrope is a salt of guanidine and, in particular, guanidine hydrochloride. Reducing agents are compounds that react with and lower the oxidation state of other compounds, for example, by reducing a cystine dimer to cysteine. A preferred reducing agent is the reduced form of dithiothreitol (DTT). A preferred pH is in the range of 7.0 to 9.5 and, in particular, a pH of approximately 8.5. This application will use the term "approximately" with respect to pH to reflect changes in pH affected by temperature, monitoring equipment and normal variations in laboratory techniques. The solution in which the reduction and denaturation step is performed comprises tris and EDTA. The terms tris and EDTA are well known in the art. "tris" refers to tris(hydroxymethyl)aminomethane and "EDTA" refers to ethylenediaminetetraacetic acid.

Preferably, folding conditions comprise removal of the chaotrope from solutions of a mixture of the first and a second subunit and an initial increase in pH to 8.5–9.5. Preferably, the pH is approximately 9.0. The initial pH is then lowered to a pH of 6.5–7.0 and, most preferably, approximately 6.7. Preferably, this change of pH is effected gradually.

Preferably, the folding is effected by conditions and changes in conditions of solutions that contain the first and second subunits, which solutions further comprise glycerol. A preferred concentration of glycerol is 5–30% (v/v) and, most preferably approximately 20% (v/v). With reference to concentrations, this application will use the term "approximately" to suggest variances due to measuring laboratory techniques and equivalents. These solutions preferably comprise tris, DTT, and EDTA. Preferably, folding conditions comprise a temperature of 0°–15° C., most preferably 4° C.

Preferably, the method comprises the step of purifying the ICE and ICE-like compositions. Purification conditions comprise the removal of particulates by centrifugation and filtration. Preferably, purification conditions further comprise chromatography, and most preferably, ion exchange chomatography. Chromatography is preferably performed in a first chromatography buffer. The buffer imposes chemical conditions on the ICE and ICE-like compositions causing the ICE or ICE-like compositions to bind noncovalently to an ion exchange resin. To effect purification of the ICE or ICE-like compositions bound to the ion-exchange resin, the ICE or ICE-like compositions are eluted selectively from the column by gradually increasing the salt concentration of the first chromatography buffer either by direct addition of salt or by gradual replacement of the first buffer with a second buffer having a greater salt concentration. Preferably the first chromatography buffer further comprises glycerol. A preferred concentration is 5–30% (v/v) glycerol and most preferably 20% (v/v). A preferred buffer comprises HEPES, and EDTA.

ICE and ICE-like compositions can be further purified to form proteins capable of crystallization. The crystallized protein can be utilized to determine the three-dimensional structure of the protein in atomic detail and thus to evaluate the binding site of substrates and inhibitors of ICE and ICE-like compositions. Crystallized ICE and ICE-like compositions have utility to design inhibitors of the enzyme.

Preferably, the method comprises the step of combining the ICE and ICE-like compositions with inhibitors of ICE to form an ICE inhibitor complex. The inhibitor stabilizes the enzyme. ICE or the ICE-like compositions with an inhibitor have utility as models for the interaction between ICE or ICE-like compositions and the substrate IL-1β.

A preferred inhibitor is acetylated N-terminus-tyrosine-valine-alanine-NH-CH-($CH_2COOH$) CO-$CH_2Cl$, where all chiral centers conform to natural L-amino acids (Ac-YVAD-CMK).

Preferably, the method comprises the step of further purification by chromatography of the ICE and ICE-like compositions with inhibitors bound.

A further embodiment of the present invention features compositions of matter. One embodiment of the present composition comprises a non-naturally occurring ICE or ICE-like composition.

As used herein, the term "non-naturally occurring" refers to an object which has been manipulated or changed from its natural state. As applied to a cell, a non-naturally occurring cell has a non-naturally occurring nucleic acid, or makes a non-naturally occurring peptide, or is fused to a cell to which it is not combined with in nature. The term "non-naturally occurring nucleic acid" refers to a portion of a genomic nucleic acid, cDNA, semi-synthetic nucleic acid or synthetic original nucleic acid which by virtue of its origin or manipulation, is not associated with all of the nucleic acid to which it is associated with in nature, or is linked to a nucleic acid or other chemical agent other than that to which it is linked in nature, or does not occur in nature. The term "non-naturally occurring peptide" refers to a portion of a larger naturally occurring peptide or protein, or semi-synthetic or synthetic peptide, which by virtue of its origin or manipulation, is not associated with all of the peptide to which it is associated in nature, or is linked to a peptide, functional group or chemical agent other than that to which it is linked in nature, or does not occur in nature.

Preferably, the non-naturally occurring ICE or ICE-like composition comprises a 12 kDa subunit and a 18 or 24 kDa subunit of ICE or an ICE-like composition which subunits are combined and folded to form a composition having ICE-like activity. Most preferably, the larger subunit is a 20 kDa subunit. Most preferably, the smaller subunit is a 10 kDa subunit. Preferably, the ICE or ICE-like composition is a recombinant protein.

A further embodiment features a non-naturally occurring ICE and ICE-like composition and an inhibitor in the form of a complex. ICE or ICE-like compositions that are part of an inhibitor-ICE complex exhibit improved stability. Such inhibitor-ICE complexes can be purified to form a composition capable of crystallization. A preferred composition comprises a crystal of an inhibitor-ICE complex.

The present invention is further described in the following figures and examples, which illustrate features of the present invention and highlight preferred embodiments and the best mode to carry out features of the present invention.

BRIEF DESCRIPTION OF THE DRAWINGS

FIG. 1 depicts a nucleotide sequence of a nucleic acid encoding the 45 kDa protein pre-ICE, also set forth as Seq. ID No. 1; and FIG. 2 depicts the amino acid sequence of a 45 kDa protein corresponding to pre-ICE, also set forth as Seq. ID No. 2.

DETAILED DESCRIPTION OF THE INVENTION

The present invention will be described in detail as methods for making ICE and ICE-like compositions, and the compositions so formed. The method comprises the steps of combining two subunits of ICE or ICE-like compositions, and imposing conditions for folding on the combined subunits to form an ICE or an ICE-like composition capable of proteolytically processing pre-IL-1β to IL-1β. The two subunits can be made synthetically or by expressing cloned nucleic acid operably linked to a suitable promoter in one or more host cells. The method further comprises the step of combining the ICE and ICE-like compositions with inhibitors of ICE to stabilize the enzyme. The method further comprises the step of further purification by chromatography of the ICE and ICE-like compositions with inhibitors bound. The compositions so formed can be purified to form crystallography-grade ICE and ICE-like compositions.

The practice of the present invention will employ, unless otherwise indicated, conventional techniques of chemistry, molecular biology, microbiology, recombinant DNA technology and immunology, which are within the skill of the art and are explained fully in the literature. See, e.g., Sambrook, Fritsch and Maniatis, *Molecular Cloning: A Laboratory Manual*, Cold Spring Harbor Laboratory Press (1989); *DNA Cloning*, Vols. 1 and 2, (D. N. Glover, Ed. 1985); *Oligonucleotide Synthesis* (M. J. Gait, Ed 1984); *Nucleic Acid Hybridization* (B. D. Hames and S. J. Higgins, Eds. 1984); The Series, *Methods In Enzymology* (Academic Press, Inc.) particularly Vol. 154 and Vol. 155 (Wu and Grossman, Eds.), and Vol. 182 (Deutscher, Ed.); Stout and Jensen, *X-ray Structure Determination, A Practical Guide* (Wiley-Interscience, 1989).

Other features of the present invention will be apparent from the following examples.

EXAMPLE 1

This example describes the cloning of nucleic acids encoding ICE, pre-ICE and ICE-like compositions. Nucleic acids encoding ICE, pre-ICE and ICE-like compositions were constructed with the use of PCR. PCR primers were designed based upon the published pre-ICE cDNA sequence as described in International Patent Number WO 91/15577, having a filing date of Apr. 4, 1991, by the Immunex Corporation, and in Thornberry et al., Nature volume 356, pages 768–774 (1992), except that some codons were altered to codons that encode the same amino acids but that are generally preferred for high-level expression in *E. coli*. This sequence is set forth in Seq. ID No. 1 and FIG. 1.

A nucleic acid corresponding to a 20 kDa subunit of an ICE-like (p20) composition was constructed with PCR using the 5' primer P1 and the 3' primer P2. This subunit of an ICE-like composition, P20, corresponds to amino acids 120–297 of the full length 45 kDa pre-ICE molecule set forth in Seq. ID No. 2 and FIG. 2 with an additional methionine residue added to the amino terminus to allow expression. A 22 kDa subunit of an ICE-like composition (p22) can be readily constructed with additional nucleotides corresponding to the 16 amino acids 104 to 120 of Seq. ID No. 2. Thus, the 22 kDa subunit comprises amino acid 104–297 of the full length 45 kDa preICE molecules, preferably with an additional methionine residue added to the amino terminus to allow expression. Although these examples feature a p20 subunit, a p22 subunit is believed to behave similarly.

A nucleic acid corresponding to a 10 kDa subunit of an ICE-like composition was constructed with PCR using the 5' primer P3 and the 3' primer P4. This ICE-like composition, p10, corresponds to amino acids 317–404 of the full length 45 kDa pre-ICE molecule, set forth in Seq. ID No. 2 as FIG. 2 with an additional methionine residue added to the amino terminus to allow expression.

Table 1, set forth below, describes primers P1 (SEQ. I.D. No. 3), P2 (SEQ. I.D. No. 4) , P3 (SEQ. I.D. No. 5) and P4 (SEQ. I.D. No. 6).

TABLE 1

| Primer | Sequence |
|--------|----------|
| P1: | 5'-GGG GAA TTC ATG AAC CCG GCT ATG CCG ACC TCT TCT GGT TCT GAA GGT AAC GTT AAA CTG TGC TCT CTG GAA GAA GC-3' |
| P2: | 5'-CCC CAC TAG TCC TCT ATT AAT CTT TAA ACC ACA CCA CAC CAG GGC-3' |
| P3: | 5'-GGG GAA TTC ATG GCT ATC AAA AAA GCT CAC ATC GAA AAA GAC TTC ATC GCT TTC TGC-3' |
| P4: | 5'-CCC CAC TAG TCC TCT ATT AAT GTC CTG GGA AGA GG-3' |

Nucleic acids encoding an in-frame initiator methionine were added to the p10 and p20 constructs by means of the 5'-primers P1 and P3. In addition, the 5' primers P1 and P3 each also contained Eco RI restriction sites. The 3' primers P2 and P4 each also contained Spe I restriction sites. In addition, the 5' primers P1 and P3 each contain several nucleic acid base changes from the natural nucleic acid sequence to give some new codons that encode the same amino acids as the natural codons but that are generally preferred codons for high level expression in *E. coli*.

A full length ICE precursor (p45) cDNA that was subcloned into a transient expression vector was used as a template to PCR-clone the p20 and p10 ICE forms. All of the ICE PCR products obtained were purified using GeneClean (Bio 101 Inc.) and subcloned undirectionally into an *E. coli* pL expression plasmid.

Transcription from a pL expression plasmid is regulated by the temperature-sensitive repressor protein $cI^{857}$ $cI^{857}$ prevents transcription at 30° C. or less and loses its ability to prevent transcription at 42° C. A nucleic acid gene encoding $cI^{857}$ is encoded on the plasmid vector pACYC177 $cI^{857}$ pACYC177 $cI^{857}$ also encodes a kanamycin resistance gene, and the plasmid is maintained by the presence of kanamycin in the culture medium. The pL expression plasmid encodes an ampicillin resistance gene, and that plasmid is maintained by the presence of ampicillin in the culture medium. pL-regulated ICE expression plasmids could be used to produce ICE proteins in any *E. coli* strain that contains an expressed $cI^{857}$ gene on any compatible plasmid or as a stable integrant in the *E. coli* chromosome.

EXAMPLE 2

This example describes the transformation of *E. coli* with nucleic acid encoding the 10 kDa subunit or the 20 kDa subunit of the mature form of ICE, operably linked to a promoter. Transformations with nucleic acid encoding other subunits including a 22 kDa subunit, would be performed in a similar manner.

Frozen competent *E. coli* were quickly thawed and placed on ice for 10 minutes. 100 μl aliquots of the cell mixture were transferred into chilled sterile polypropylene tubes. Supercoiled plasmid DNA (1 ng) was added to the competent cells and the tubes were gently swirled to mix the contents. The cells were heat shocked by transferring the tubes into a 37° C. circulating water bath for exactly 2 minutes and then quickly transferred to ice. Next, 1 ml of 2×YT medium was added to each tube. The tubes were shaken at 225 cycles per minute at 30° C. for 1 hour. The transformed cells were transferred to LB agar plates with ampicillin and kanamycin. After incubation overnight at 30° C. the transformed cells were selected and grown up in 2×YT medium at 30° C.

EXAMPLE 3

This example describes the induction of cells transformed with a gene encoding a subunit of ICE or an ICE-like composition to transcribe and translate an ICE protein subunit from those genes. Cells transformed as described in Example 2 were used to inoculate a 12.5 liter culture of EC3 medium at 29° C. EC3 medium was prepared by dissolving 225 g Difco tryptone, 75 g Difco yeast extract, 48 g $K_2HPO_4$, 30 g $(NH_4)_2SO_4$, 12 g $NaH_2PO_4$, 1.5 g ampicillin, and 0.75 g kanamycin in 12.5 liters of deionized water, and autoclaved to effect sterilization. The pH of the solution was monitored continuously during the fermentation and was maintained at no less than 6.8 during the fermentation by addition of 15% $NH_4OH$ as needed. A solution of 1.2 liters of EC3A medium was added gradually throughout the fermentation and induction periods. EC3A medium was prepared by dissolving 2.05 g $Fe_2(SO_4)_3 \cdot 8H_2O$, 0.92 g $Zn(NO_3)_2 \cdot 6H_2O$, 0.83 g $CaCl_2 \cdot 2H_2O$, 0.26 g $MnCl_2 \cdot 4H_2O$, 116 mg $CuCl_2 \cdot 2H_2O$, 5 g citric acid monohydrate, 67 mg $H_3BO_3$, 67 mg $COCl_2 \cdot 6H_2O$, 67 mg $Na_2MoO_4 \cdot 2H_2O$, 750 g Glycerine USP, and 37.5 g $MgSO_4 \cdot 7H_2O$ in 1.2 liters of deionized water, and the solution was autoclaved to effect sterilization.

When the $OD_{600}$ value of the culture reached 30, the temperature of the culture was raised to 42° C. to induce transcription and translation of the genes encoding ICE or ICE-like compositions. One hour prior to induction and throughout the induction period, a solution of 1 liter of EC3B medium was added gradually. EC3B medium was prepared by dissolving 100 g Difco tryptone, 50 g Difco yeast extract, and 5.0 g NaCl in 1 liter of deionized water, and autoclaved to effect sterilization, 4 hours after induction the cells were harvested by concentration using a Millipore Pellicon filter unit with a 0.2 μm tangential filtered, followed by centrifugation at 12,000×g. The supernatant was removed, and the cell pellets were stored at −80° C.

EXAMPLE 4

This example describes the preparation of cells transformed with a gene encoding a subunit of ICE or an ICE-like composition and induced to transcribe that subunit of ICE or an ICE-like composition for isolation of the subunit.

The cell paste prepared as described in Example 3 was placed in centrifuge tubes, thawed, and thereafter placed on ice. Seven volumes of Buffer A (compared to the volume of the pellet), comprising 2% Triton X-100 and 50 mM tris (pH 8.0), was added to each centrifuge tube. The pellet was homogenized by sonication. The homogenized pellet was passed through a microfluidizer twice at 4° C., and the microfluidizer was flushed with one additional volume of Buffer A. The mixture was examined under a microscope, and passed through a microfluidizer once again, if necessary.

The sample was then diluted to 5.5 liters with additional Buffer A, and allowed to incubate at room temperature with stirring for 60 minutes. This sample was then centrifuged 12,000×g for 20 minutes at room temperature. The supernatant was discarded, and the pellet was resuspended in an equivalent volume of Buffer A at 4° C. The steps of homogenization, incubation, and centrifugation were then repeated twice.

Next, the process of homogenization, incubation, and centrifugation was repeated three times using Buffer B at 4° C., comprising 500 mM NaCl, 50 mM tris (pH 8.0).

Next, the process of homogenization, incubation, and centrifugation was repeated once using Buffer C at 4° C., comprising 50 mM tris 8.0.

Aliquots of the sample so prepared were chromatographed on a SDS-polyacrylamide gel. The gel was stained with Coomassie Blue and read to provide an estimate of the purity of the material and an estimate of the amount of protein in the pellet.

EXAMPLE 5

This example describes the solution of subunits of ICE and ICE compositions. Protein subunits of ICE or an ICE-like composition in the form of inclusion bodies prepared as described in Example 4 were solvated in a denatured form and reduced in a solution comprising 6M GuHCl, tris 200 mM DTT and 50 mM tris (pH 8.5) for 24 hours. Samples containing the 10 kDa subunit were prepared to a protein concentration of 1 mg/ml. Samples containing the 20 kDa subunit were prepared to a protein concentration of 2 mg/ml.

The solubilized denatured and reduced protein was dialysed at room temperature against 10 volumes of 5% (v/v) acetic acid, three times for at least three hours each. Following dialysis the samples were centrifuged at 7,000×g for 40 min. The supernatant was then filtered with a 0.22 μm filter. The filtrate is suitable for HPLC purification.

EXAMPLE 6

This example describes combining a separately expressed 10 kDa subunit and a 20 kDa subunit and folding such subunits to form ICE or ICE-like compositions. These subunits, which in separate solutions have been subjected to denaturation and renaturation as described in the previous Example, do not form an active ICE or ICE-like composition. Such subunits must be subjected to renaturation together to form an active ICE or an ICE-like composition. Other subunits having a similar size to the 10 or 20 subunit, may be combined and folded under similar conditions.

Two cell extracts of Example 5, one comprising the 10 kDa subunit and one comprising the 20 kDa subunit of ICE, were dissolved in separate solutions of 6M GuHCl and 200 mM DTT, at pH 8.5. The extracts containing each subunit were solubilized to a concentration of approximately 2 mg/ml (100–200 nM). The concentrations of these protein solutions were measured by quantitative amino acid analysis. Other techniques for the measurement of protein concentration in solution, such as colorimetric assays, could also be used. The solubilized proteins can be stored at −80° C., if not further processed immediately.

The solutions containing the proteins were next subjected to protein denaturing conditions. Preferred conditions were imposed by diluting solutions containing the 10 kDa subunit and the solution containing the 20 kDa subunit, each to 1 mg/ml, in 6M GuHCl, 25 mM tris, 200 mM DTT, 0.5 mM EDTA, at pH 8.5, and incubating for 18–24 hours at room temperature.

A low concentration tris buffer is preferred over higher concentrations. A 10 mM tris buffer produced yields of active enzyme of up to 2 fold over 100 mM tris buffers.

Next, the solutions containing the denatured 10 kDa or 20 kDa subunits were mixed and diluted to final concentrations of 16.7 µg/ml of 10 kDa subunit and 33 µg/ml 20 kDa subunit in 6M GuHCl, 25 mM tris (pH 9.0), 5 mM DTT, and 0.5 mM EDTA.

Other chaotropes may be substituted for guanidine hydrochloride. The concentration of 6M GuHCl is a preferred concentration. A range of 2.0 to 8.0M may be acceptable.

The buffer solutions comprising tris, DTT and EDTA are preferred buffers. Other buffers capable of pH 8.5 may be substituted for such buffer solutions. The tris component provides an improved yield of approximately three to four fold over phosphate and HEPES based buffers.

A total protein concentration of 10 to 1000 µg/ml is acceptable. Preferably, the total protein concentration is less than 200 µg/ml to avoid precipitation of protein. The 10 and 20 kDa subunits are combined in a 1:1 molar ratio.

The combined subunits were dialyzed, in dialysis tubing (Spectra-Pot 1, 6–8000 MWCO, 1 ml/cm) against 100 volumes of a solution comprising 25 mM tris, 5 mM DTT, 0.5 mM EDTA, pH, 9.0, at 4° C., for 3 hours. The dialysis buffer is constantly stirred. The temperature of 4° C. is a preferred temperature. Lower temperatures may not be possible due to freezing. Higher temperatures may result in a lower yield of active ICE enzyme. A temperature of 22° C. is associated with a two-fold reduction in yield of active ICE enzyme.

A pH of 9.0 is a preferred pH. A pH of above 9.0 may result in unwanted chemical reactions. A pH of 7.5 or lower may reduce the yield of active ICE enzyme as much as 50%. The buffer solution of tris, DTT and EDTA is preferred buffer. Other buffers capable of pH 9.0 may be substituted for the buffer solution. The tris component provides an improved yield of approximately three to four fold over phosphate and HEPES-based buffers.

The dialysis process was repeated for an additional three hours with fresh dialysis buffer and again for 14 hours with fresh dialysis buffer.

Next, the combined subunits were dialyzed against 100 volumes of a new dialysis buffer comprising 20% (v/v) glycerol, 100 mM HEPES, 5 mM DTT, 0.5 mM EDTA, pH 6.7, for 2 hours. The combined and folded subunits were redialyzed with fresh buffer of the same composition for one hour. During this final dialysis, the activity of the sample was monitored every thirty minutes. The protein solution was then removed from dialysis tubing and adjusted to a pH value of 7.0 at 4° C. with 2M HEPES (which is itself not pH adjusted). The protein solution was centrifuged at 2,200 ×g for 30 minutes at 4° C., and filtered at 0.2 µm.

Other non-denaturing alcohols and sugars can be substituted for glycerol. However, such other alcohols and sugars may be associated with a reduction in yield. By way of example, sucrose and sorbitol in 20% (w/v) concentrations may result in a 30% reduction in activity compared to glycerol. The presence of glycerol or other non-denaturing alcohols and sugars, is associated with a two fold increase over processes without such compositions.

Chaotropes are removed in a gradual manner to improve yield. Stepped removal of chaotropic salts, through dilutions, is associated with decreased yield. A pH of 6.7 for the final dialysis is a preferred pH. Use of a pH of 6.5–7.0 is associated with an improved yield of compound over the maintenance of an elevated pH.

The HEPES buffer is a preferred buffer. The HEPES buffer is associated with a 30–40% greater yield over a process maintaining a tris buffer.

The time for completing dialysis is a compromise between improved yields and autocatalytic degradation of the ICE or ICE-like composition. A period of time of 2–5 hours generally produces acceptable yields.

EXAMPLE 7

This Example features the purification of ICE or an ICE-like composition after the composition has been formed by combining and folding two subunits as described in Example 6.

The dialyzed material of Example 6 was centrifuged at 2,200×g for 30 minutes at 4° C., and filtered (at 0.2 µm.

A FPLC ion-exchange column (MonoS HR16/10, 20 ml bed volume) was pre-equilibrated with Buffer A at 4° C. Buffer A comprises 50 mM HEPES pH 6.7 (pH at 21° C.), 20% (v/v) glycerol, and 0.5 mM EDTA.

The filtered material was applied to the FPLC column at a flow rate of about 5 ml/min. The column was then washed with Buffer A until a stable baseline was achieved. The buffer was then modified to constitute 84% Buffer A and 16% Buffer B, to increase the salt concentration. Buffer B comprises 100 mM HEPES pH 6.7 (pH at 21° C.), 20% (v/v) glycerol, 500 mM NaCl, and 0.5 mM EDTA. Free 20 kDa ICE protein and other contaminants eluted and appeared as large peaks in a trace of the absorbence of the eluate monitored at 280 nm. The wash was continued until a stable baseline was established.

Next, the buffer was again modified to constitute 70% Buffer A and 30% Buffer B over 5 ml. The major peak that eluted, observed by changes in absorbence at 280 nm of the eluate, contained active enzyme containing 10 kDa and 20 kDa fragments at a 1:1 molar ratio. A contaminant peak of enzymatically inactive free 10 kDa eluted after the peak containing active enzyme. The major peak eluted in approximately 40–80 ml. A small aliquot was assayed for activity. A recovery of activity of 50–80% is normal.

In this example, a salt concentration of 80 mM is a preferred salt concentration. Solutions with salt concentrations above or below 80 mM NaCl may result in less efficient separation of folded protein and inactive protein.

EXAMPLE 8

This Example features the purified ICE-like composition combined with a stabilizing inhibitor and further purification thereof. The purified ICE-like composition was combined with acetyl-Tyrosine-Valine-Alanine-NH-CH(CH$_2$COOH)CO-CH$_2$Cl, where all chiral centers conform to natural L-amino acids (Ac-YVAD-CMK). This inhibitor is maintained as a 10 mM solution in dimethylsulfoxide (DMSO).

An aliquot of 75 μl of inhibitor solution was added to 50 ml of the purified protein of Example 6. Additional 50 μl aliquots of inhibitor solution were added every 30 minutes for 4 total applications (225 μl). The combined inhibitor-ICE composition was then assayed for ICE activity. The enzyme, so inhibited, normally will display only background activity.

The inhibitor-ICE composition is dialyzed in dialysis tubing (Spectra-Por 1, 6–8000 MWCO, 1 ml) against 200 volumes of a solution comprising 50 mM HEPES pH 6.5 (pH at 21° C.), 20% (v/v) glycerol, 0.5 mM EDTA, 0.5 mM DTT, for approximately 16 hours at approximately 4° C. The presence of salt in Buffer C or in the solutions containing the ICE-inhibitor complex may result in inefficient binding of the ICE-inhibitor complex to the FPLC column described below.

Precipitates were removed by filtering at 0.2 μm. An ion exchange column (MonoS HR 10/10, 8 ml bed volume) was preequilibrated with Buffer C at about 4° C. Buffer C comprises 50 mM HEPES PH 6.5 (measured at 21° C.). The protein filtrate was applied to the ion exchange column at a flow rate of about 2 ml/min. The column was washed with Buffer C until a stable baseline was achieved. The buffer was modified to constitute 91% Buffer C, and 9% Buffer D over 10 ml, to increase the salt concentration. Buffer D comprises 100 mM HEPES pH 6.5 (at 21° C.), and 500 mM NaCl. The first peak, observed by changes in absorbence of the eluate at 280 nm, was the inhibited enzyme. The protein yield was estimated by integrating the peak. Approximately 1 absorbence unit at 280 nm wavelength per ml of eluate corresponds to 1.2 mg of inhibited protein.

Dry ammonium sulfate was applied to the solutions at 516 mg/ml (80% of saturation at 0° C.), and the solutions were maintained at 0° C. for 30 minutes, to form a protein precipitant. Thereafter, the solutions and precipitants were centrifuged at 2,200×g for 30 minutes.

The pellet was redissolved in a minimal volume of a solution of 20 mM acetate pH 5.0, purged with nitrogen. The Ac-YVAD-CMK inhibitor was added to a final 6-fold molar excess over ICE protein. The inhibitor and protein were stored at −80° C. This solution was diluted directly into crystalization trial solutions.

EXAMPLE 9

This Example features crystallization of ICE or an ICE-like composition in complex with the inhibitor Ac-YVAD-CMK after the composition has been prepared as described in Example 8.

Crystals of ICE or an ICE-like composition in complex with the inhibitor Ac-YVAD-CMK were grown using the sitting drop variant of the vapor diffusion method. A volume of 2 μl of a solution of ICE or an ICE-like composition in complex with the inhibitor Ac-YVAD-CMK in 20 mM acetate pH 5.0, prepared as described in Example 8, was pipetted onto a polystyrene "bridge" containing a smooth hemispherical depression. The bridge was placed in one well of a multi-well tissue culture plate which well contained about 700 μl of a precipitation and buffer solution. The composition of the precipitation and buffer solution is described below. A volume of 2μl of the precipitation and buffer solution was added to the solution of ICE or an ICE-like composition in complex with the inhibitor Ac-YVAD-CMK. The well of the tissue culture plate was covered with a glass microscope coverslip using silicone grease to form an air-tight seal. The plate was incubated at 4° C., undisturbed, for seven days or more, to effect formation of crystals of ICE or an ICE-like composition in complex with the inhibitor Ac-YVAD-CMK.

A concentration of ICE or an ICE-like composition in complex with the inhibitor Ac-YVAD-CMK in 20 mM acetate pH 5.0, of about 2 to 6 mg/ml, is a preferred concentration, and a concentration of 3.5 mg/ml is most preferable for the formation of crystals.

Precipitation and buffer solutions comprising 200 mM MgCl$_2$, 30% (w/v) polyethylene glycol 4000, and 0.1M tris, pH 8.4; or comprising 1.4M sodium acetate and 100 mM sodium cacodylate, pH 6.5; or comprising 200 mM sodium acetate, 30% (w/v) polyethylene glygol 4000, and 100 mM sodium citrate, pH 5.6; or comprising 200 mM magnesium acetate, 20% (w/v) polyethylene glycol 8000, and 100 mM sodium cacolylate, pH 6.5 are preferred. Variants on these conditions will give rise to crystals, but of a smaller size.

Crystals of ICE or an ICE-like composition in complex with the inhibitor Ac-YVAD-CMK prepared using preferred conditions described above displayed bipyramidal morphology. Crystals so obtained typically measured 0.5 mm between the most distant apexes and 0.25 mm between any two of the remaining four neighboring apexes.

EXAMPLE 10

This Example features X-ray diffraction by crystals of ICE or an ICE-like composition in complex with the inhibitor Ac-YVAD-CMK, prepared as described in Example 9, and demonstration that the crystals so obtained diffract X-rays to high resolution.

Using a source of X-rays generated by a copper rotating anode run at 4.5 kW and with a 0.3×0.3 mm focal spot, crystals of ICE or an ICE-like composition in complex with the inhibitor Ac-YVAD-CMK prepared as described in Example 9 diffracted X-rays with a minimum interplanar spacing of less than 2.4 A. The X-ray diffraction data revealed that the crystals displayed the standard space group P4(3)2(1)2. The X-ray diffraction data also revealed that the crystals displayed unit cell dimensions of a=b=64.6±0.3A, c=161.6±1.0A. Protein crystal diffration data to 2.4A and less is regarded in the art as high resolution, and is regarded that it can be used to determine a protein structure of sufficient quality and resolution to be of substantial utility in inhibitor design.

The quality of the atomic structure that can be obtained from a crystallized protein is limited by the diffraction quality of the crystals from which diffraction data are determined. Growth of high quality crystals is limited by the purity of the protein with respect to contaminants, as well as by conformational homogeneity. Growth of crystals that diffract to high resolution demonstrates that the method by which the protein was prepared is of substantial utility for protein crystallization and structure determination.

Thus, while preferred embodiments have been illustrated and described, it is understood that the present invention is capable of variation and modification and, therefore, should not be limited to the precise details set forth, but should include such changes and alterations that fall within the purview of the following claims.

We claim:

1. A method of making interleukin-1 beta converting enzyme (ICE) or ICE-like compositions having a first subunit and a second subunit, comprising the steps:

(a) combining denatured first and second subunits to form an admixture of said first and second subunits;

(b) imposing folding conditions for folding the first and second subunits in said admixture to form an ICE or ICE-like composition.

2. The method of claim 1 wherein said first subunit comprises a 10 to 12 kDa subunit of ICE, selected from amino acids 298 to 404 of Seq. ID No. 2.

3. The method of claim 1 wherein said second subunit comprises a 18 to 24 kDa subunit of ICE, selected from amino acids 104 to 316 of Seq. ID No. 2.

4. The method of claim 1 wherein said first and second subunit are denatured prior to combining the subunits.

5. The method of claim 4 wherein said first and second subunit are denatured in chaotropic solutions.

6. The method of claim 5 wherein said chaotropic solution comprises a guanidine salt.

7. The method of claim 4 wherein said first and second subunit are denatured in a solution having a pH of approximately 8.0–9.0.

8. The method of claim 4 wherein said first and second subunit are denatured in a solution of guanidine hydrochloride, tris, DTT and EDTA.

9. The method of claim 1 wherein said folding conditions comprise an initial solution pH of approximately 8.0–9.5.

10. The method of claim 1 wherein said folding conditions comprise a temperature of 4° C.

11. The method of claim 1 wherein said folding conditions comprise removal of a chaotrope.

12. The method of claim 9 wherein said folding conditions comprise a change from said initial solution pH to a pH of 6.5–7.

13. The method of claim 1 wherein said folding conditions comprise buffered solutions comprising glycerol.

14. The method of claim 1 wherein said folding conditions comprise removal of chaotrope from said admixture by maintaining said admixture in a first buffered solution having a pH of 8.5–9.5 and then changing to a second buffered solution having a pH of 6.5–7.0, a glycerol concentration of 5–30% (v/v) and a temperature of 4° C.

15. The method of claim 14 wherein said admixture is maintained in said first buffered solution comprising tris, DTT, and EDTA, having a pH of 8.5–9.5 and said second buffered solution comprising HEPES, DTT and EDTA, 5–30% (v/v) glycerol and a pH of 6.5–7.0.

16. The method of claim 1 wherein said first and second subunits are expressed in a procaryotic cell.

17. The method of claim 16 wherein said procaryotic cell is *Escherichia coli*.

18. The method of claim 16 wherein said first subunit is expressed in a first cell and said second subunit is expressed in a second cell.

19. The method of claim 18 wherein said first subunit is expressed by a cell transformed with a nucleic acid operably linked to a promoter, said nucleic acid comprising sequences 358 to 891 of Seq. ID No. 1.

20. The method of claim 18 wherein said second subunit is expressed by a cell transformed with a nucleic acid operably linked to a promoter comprising sequences 994 to 1212 of Seq. ID No. 1.

21. The method of claim 1 further comprising the step of imposing purification conditions on the ICE or ICE-like composition.

22. The method of claim 21 wherein said purification conditions comprises removal of particulates.

23. The method of claim 22 wherein said particulates are removed with filtration and/or centrifugation.

24. The method of claim 21 wherein said purification conditions comprise chromatography.

25. The method of claim 24 wherein said chromatography is by ion exchange chromatography.

26. The method of claim 24 wherein said chromatography is fast protein liquid chromatography.

27. The method of claim 26 wherein said fast protein liquid chromatography is performed in a first chromatography buffer having salt concentration of 0–5 mM and said salt concentration is increased after a stable baseline is achieved.

28. The method of claim 27 wherein said first buffer comprises HEPES, 10–30% (v/v) glycerol and EDTA.

29. The method of claim 27 wherein said salt is sodium chloride.

30. The method of claim 1 further comprising the step of forming an inhibitor-ICE composition, said inhibitor-ICE composition formed by making an admixture of said ICE or ICE-like composition with an inhibitor of ICE or ICE-like compositions.

31. The method of claim 30 wherein salt is removed from the inhibitor-ICE composition by dialysis.

32. The method of claim 30 wherein said inhibitor-ICE composition is purified by chromatography.

33. The method of claim 32 wherein said chromatography is ion exchange chromatography.

34. The method of claim 33 wherein said ion exchange chromatography is fast protein liquid chromatography.

35. The method of claim 34 wherein said chromatography is performed in a buffer comprising a first buffer and a second buffer, said second buffer having a salt concentration greater than said first buffer, said buffer comprising said first buffer initially until a baseline is established and thereafter increasing in said second buffer to form a salt gradient to elute said inhibitor ICE composition.

36. The method of claim 35 wherein said first buffer is 50 mM HEPES at a pH of 6.0–7.0 and said second buffer is 100 mM HEPES at a pH of 6.0–7.0 and 500 mM NaCl.

37. The method of claim 36 wherein said buffer is comprised initially of said first buffer, which first buffer is diluted with said second buffer to a concentration of 91% first buffer and 9.0% second buffer.

38. The method of claim 30 wherein ICE inhibitor complex is purified by precipitation.

39. The method of claim 38 wherein said precipitation is effected with dry ammonium sulfate.

40. The method of claim 30 further comprising forming crystals of said inhibitor-ICE composition.

41. A non-naturally occurring recombinant interleukin-1 beta converting enzyme (ICE) or ICE-like composition comprising two subunits, at least one of said subunits being produced in procaryotic cells, which subunits are denatured, combined and folded to form said non-naturally occurring ICE or ICE-like composition.

42. The composition of claim 41 wherein said ICE or ICE-like composition has a 10 to 12 kDa subunit and an 18 to 24 kDa subunit which are separately expressed by a procaryotic cell.

43. The composition of claim 41 further comprising an inhibitor complexed to said ICE or ICE-like composition to form a inhibitor-ICE complex.

44. The composition of claim 43 where said inhibitor-ICE complex has a purity, which purity allows said inhibitor ICE complex to form crystals.

45. A crystal comprising interleukin-1 beta converting enzyme (ICE) or an ICE-like composition complexed to an ICE inhibitor.

46. The composition of claim 45 wherein said inhibitor is acetyl-Tyrosine-Valine-Alanine-NH-CH(CH$_2$COOH)CO-CH$_2$Cl, where all chiral centers conform to natural L-amino acids.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1215 base pairs
( B ) TYPE: nucleic acid
( C ) STRANDEDNESS: single
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Homo sapiens ( i x ) FEATURE:
( A ) NAME/KEY: CDS
( B ) LOCATION: 1..1215

( x i ) SEQUENCE DESCRIPTION: SEQ ID NO:1:

| ATG | GCC | GAC | AAG | GTC | CTG | AAG | GAG | AAG | AGA | AAG | CTG | TTT | ATC | CGT | TCC | 48 |
|---|---|---|---|---|---|---|---|---|---|---|---|---|---|---|---|---|
| Met | Ala | Asp | Lys | Val | Leu | Lys | Glu | Lys | Arg | Lys | Leu | Phe | Ile | Arg | Ser | |
| 1 | | | | 5 | | | | | 10 | | | | | 15 | | |

| ATG | GGT | GAA | GGT | ACA | ATA | AAT | GGC | TTA | CTG | GAT | GAA | TTA | TTA | CAG | ACA | 96 |
|---|---|---|---|---|---|---|---|---|---|---|---|---|---|---|---|---|
| Met | Gly | Glu | Gly | Thr | Ile | Asn | Gly | Leu | Leu | Asp | Glu | Leu | Leu | Gln | Thr | |
| | | | 20 | | | | | 25 | | | | | 30 | | | |

| AGG | GTG | CTG | AAC | AAG | GAA | GAG | ATG | GAG | AAA | GTA | AAA | CGT | GAA | AAT | GCT | 144 |
|---|---|---|---|---|---|---|---|---|---|---|---|---|---|---|---|---|
| Arg | Val | Leu | Asn | Lys | Glu | Glu | Met | Glu | Lys | Val | Lys | Arg | Glu | Asn | Ala | |
| | | 35 | | | | | 40 | | | | | 45 | | | | |

| ACA | GTT | ATG | GAT | AAG | ACC | CGA | GCT | TTG | ATT | GAC | TCC | GTT | ATT | CCG | AAA | 192 |
|---|---|---|---|---|---|---|---|---|---|---|---|---|---|---|---|---|
| Thr | Val | Met | Asp | Lys | Thr | Arg | Ala | Leu | Ile | Asp | Ser | Val | Ile | Pro | Lys | |
| | 50 | | | | | 55 | | | | | 60 | | | | | |

| GGG | GCA | CAG | GCA | TGC | CAA | ATT | TGC | ATC | ACA | TAC | ATT | TGT | GAA | GAA | GAC | 240 |
|---|---|---|---|---|---|---|---|---|---|---|---|---|---|---|---|---|
| Gly | Ala | Gln | Ala | Cys | Gln | Ile | Cys | Ile | Thr | Tyr | Ile | Cys | Glu | Glu | Asp | |
| 65 | | | | | 70 | | | | | 75 | | | | | 80 | |

| AGT | TAC | CTG | GCA | GGG | ACG | CTG | GGA | CTC | TCA | GCA | GAT | CAA | ACA | TCT | GGA | 288 |
|---|---|---|---|---|---|---|---|---|---|---|---|---|---|---|---|---|
| Ser | Tyr | Leu | Ala | Gly | Thr | Leu | Gly | Leu | Ser | Ala | Asp | Gln | Thr | Ser | Gly | |
| | | | | 85 | | | | | 90 | | | | | 95 | | |

| AAT | TAC | CTT | AAT | ATG | CAA | GAC | TCT | CAA | GGA | GTA | CTT | TCT | TCC | TTT | CCA | 336 |
|---|---|---|---|---|---|---|---|---|---|---|---|---|---|---|---|---|
| Asn | Tyr | Leu | Asn | Met | Gln | Asp | Ser | Gln | Gly | Val | Leu | Ser | Ser | Phe | Pro | |
| | | | 100 | | | | | 105 | | | | | 110 | | | |

| GCT | CCA | CAG | GCA | GTG | CAG | GAC | AAC | CCG | GCT | ATG | CCG | ACC | TCT | TCT | GGT | 384 |
|---|---|---|---|---|---|---|---|---|---|---|---|---|---|---|---|---|
| Ala | Pro | Gln | Ala | Val | Gln | Asp | Asn | Pro | Ala | Met | Pro | Thr | Ser | Ser | Gly | |
| | | 115 | | | | | 120 | | | | | 125 | | | | |

| TCT | GAA | GGT | AAC | GTT | AAA | CTG | TGC | TCT | CTG | GAA | GAA | GCT | CAA | AGG | ATA | 432 |
|---|---|---|---|---|---|---|---|---|---|---|---|---|---|---|---|---|
| Ser | Glu | Gly | Asn | Val | Lys | Leu | Cys | Ser | Leu | Glu | Glu | Ala | Gln | Arg | Ile | |
| | 130 | | | | | 135 | | | | | 140 | | | | | |

| TGG | AAA | CAA | AAG | TCG | GCA | GAG | ATT | TAT | CCA | ATA | ATG | GAC | AAG | TCA | AGC | 480 |
|---|---|---|---|---|---|---|---|---|---|---|---|---|---|---|---|---|
| Trp | Lys | Gln | Lys | Ser | Ala | Glu | Ile | Tyr | Pro | Ile | Met | Asp | Lys | Ser | Ser | |
| 145 | | | | | 150 | | | | | 155 | | | | | 160 | |

| CGC | ACA | CGT | CTT | GCT | CTC | ATT | ATC | TGC | AAT | GAA | GAA | TTT | GAC | AGT | ATT | 528 |
|---|---|---|---|---|---|---|---|---|---|---|---|---|---|---|---|---|
| Arg | Thr | Arg | Leu | Ala | Leu | Ile | Ile | Cys | Asn | Glu | Glu | Phe | Asp | Ser | Ile | |

|  |  |  |  |  |  |  |  |  |  |  |  |  |  |  |  |
|---|---|---|---|---|---|---|---|---|---|---|---|---|---|---|---|
| | | | | 165 | | | | | 170 | | | | | 175 | |

| CCT | AGA | AGA | ACT | GGA | GCT | GAG | GTT | GAC | ATC | ACA | GGC | ATG | ACA | ATG | CTG | 576 |
|---|---|---|---|---|---|---|---|---|---|---|---|---|---|---|---|---|
| Pro | Arg | Arg | Thr | Gly | Ala | Glu | Val | Asp | Ile | Thr | Gly | Met | Thr | Met | Leu | |
| | | 180 | | | | | 185 | | | | 190 | | | | | |

| CTA | CAA | AAT | CTG | GGG | TAC | AGC | GTA | GAT | GTG | AAA | AAA | AAT | CTC | ACT | GCT | 624 |
| Leu | Gln | Asn | Leu | Gly | Tyr | Ser | Val | Asp | Val | Lys | Lys | Asn | Leu | Thr | Ala | |
| | | 195 | | | | | 200 | | | | 205 | | | | | |

| TCG | GAC | ATG | ACT | ACA | GAG | CTG | GAG | GCA | TTT | GCA | CAC | CGC | CCA | GAG | CAC | 672 |
| Ser | Asp | Met | Thr | Thr | Glu | Leu | Glu | Ala | Phe | Ala | His | Arg | Pro | Glu | His | |
| | 210 | | | | | 215 | | | | | 220 | | | | | |

| AAG | ACC | TCT | GAC | AGC | ACG | TTC | CTG | GTG | TTC | ATG | TCT | CAT | GGT | ATT | CGG | 720 |
| Lys | Thr | Ser | Asp | Ser | Thr | Phe | Leu | Val | Phe | Met | Ser | His | Gly | Ile | Arg | |
| 225 | | | | | 230 | | | | | 235 | | | | | 240 | |

| GAA | GGC | ATT | TGT | GGG | AAG | AAA | CAC | TCT | GAG | CAA | GTC | CCA | GAT | ATA | CTA | 768 |
| Glu | Gly | Ile | Cys | Gly | Lys | Lys | His | Ser | Glu | Gln | Val | Pro | Asp | Ile | Leu | |
| | | | | 245 | | | | | 250 | | | | | 255 | | |

| CAA | CTC | AAT | GCA | ATC | TTT | AAC | ATG | TTG | AAT | ACC | AAG | AAC | TGC | CCA | AGT | 816 |
| Gln | Leu | Asn | Ala | Ile | Phe | Asn | Met | Leu | Asn | Thr | Lys | Asn | Cys | Pro | Ser | |
| | | | 260 | | | | | 265 | | | | | 270 | | | |

| TTG | AAG | GAC | AAA | CCG | AAG | GTG | ATC | ATC | ATC | CAG | GCC | TGC | CGT | GGT | GAC | 864 |
| Leu | Lys | Asp | Lys | Pro | Lys | Val | Ile | Ile | Ile | Gln | Ala | Cys | Arg | Gly | Asp | |
| | | 275 | | | | | 280 | | | | | 285 | | | | |

| AGC | CCT | GGT | GTG | GTG | TGG | TTT | AAA | GAT | TCA | GTA | GGA | GTT | TCT | GGA | AAC | 912 |
| Ser | Pro | Gly | Val | Val | Trp | Phe | Lys | Asp | Ser | Val | Gly | Val | Ser | Gly | Asn | |
| | 290 | | | | | 295 | | | | | 300 | | | | | |

| CTA | TCT | TTA | CCA | ACT | ACA | GAA | GAG | TTT | GAG | GAT | GAT | GCT | ATC | AAA | AAA | 960 |
| Leu | Ser | Leu | Pro | Thr | Thr | Glu | Glu | Phe | Glu | Asp | Asp | Ala | Ile | Lys | Lys | |
| 305 | | | | | 310 | | | | | 315 | | | | | 320 | |

| GCT | CAC | ATC | GAA | AAA | GAC | TTC | ATC | GCT | TTC | TGC | TCT | TCC | ACA | CCA | GAT | 1008 |
| Ala | His | Ile | Glu | Lys | Asp | Phe | Ile | Ala | Phe | Cys | Ser | Ser | Thr | Pro | Asp | |
| | | | | 325 | | | | | 330 | | | | | 335 | | |

| AAT | GTT | TCT | TGG | AGA | CAT | CCC | ACA | ATG | GGC | TCT | GTT | TTT | ATT | GGA | AGA | 1056 |
| Asn | Val | Ser | Trp | Arg | His | Pro | Thr | Met | Gly | Ser | Val | Phe | Ile | Gly | Arg | |
| | | | 340 | | | | | 345 | | | | | 350 | | | |

| CTC | ATT | GAA | CAT | ATG | CAA | GAA | TAT | GCC | TGT | TCC | TGT | GAT | GTG | GAG | GAA | 1104 |
| Leu | Ile | Glu | His | Met | Gln | Glu | Tyr | Ala | Cys | Ser | Cys | Asp | Val | Glu | Glu | |
| | | 355 | | | | | 360 | | | | | 365 | | | | |

| ATT | TTC | CGC | AAG | GTT | CGA | TTT | TCA | TTT | GAG | CAG | CCA | GAT | GGT | AGA | GCG | 1152 |
| Ile | Phe | Arg | Lys | Val | Arg | Phe | Ser | Phe | Glu | Gln | Pro | Asp | Gly | Arg | Ala | |
| | 370 | | | | | 375 | | | | | 380 | | | | | |

| CAG | ATG | CCC | ACC | ACT | GAA | AGA | GTG | ACT | TTG | ACA | AGA | TGT | TTC | TAC | CTC | 1200 |
| Gln | Met | Pro | Thr | Thr | Glu | Arg | Val | Thr | Leu | Thr | Arg | Cys | Phe | Tyr | Leu | |
| 385 | | | | | 390 | | | | | 395 | | | | | 400 | |

| TTC | CCA | GGA | CAT | TAA | | | | | | | | | | | | 1215 |
| Phe | Pro | Gly | His | * | | | | | | | | | | | | |
| | | | | 405 | | | | | | | | | | | | |

(2) INFORMATION FOR SEQ ID NO:2:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:2:

| Met | Ala | Asp | Lys | Val | Leu | Lys | Glu | Lys | Arg | Lys | Leu | Phe | Ile | Arg | Ser |
|---|---|---|---|---|---|---|---|---|---|---|---|---|---|---|---|
| 1 | | | | 5 | | | | | 10 | | | | | 15 | |

| Met | Gly | Glu | Gly | Thr | Ile | Asn | Gly | Leu | Leu | Asp | Glu | Leu | Leu | Gln | Thr |
| | | | 20 | | | | | 25 | | | | | 30 | | |

| | | | | | | | | | | | | | |
|---|---|---|---|---|---|---|---|---|---|---|---|---|---|
| Arg | Val | Leu<br>35 | Asn | Lys | Glu | Glu | Met<br>40 | Glu | Lys | Val | Lys<br>45 | Arg | Glu | Asn | Ala |
| Thr | Val<br>50 | Met | Asp | Lys | Thr | Arg<br>55 | Ala | Leu | Ile | Asp | Ser<br>60 | Val | Ile | Pro | Lys |
| Gly<br>65 | Ala | Gln | Ala | Cys | Gln<br>70 | Ile | Cys | Ile | Thr | Tyr<br>75 | Ile | Cys | Glu | Glu | Asp<br>80 |
| Ser | Tyr | Leu | Ala | Gly<br>85 | Thr | Leu | Gly | Leu | Ser<br>90 | Ala | Asp | Gln | Thr | Ser<br>95 | Gly |
| Asn | Tyr | Leu | Asn<br>100 | Met | Gln | Asp | Ser | Gln<br>105 | Gly | Val | Leu | Ser<br>110 | Ser | Phe | Pro |
| Ala | Pro | Gln<br>115 | Ala | Val | Gln | Asp | Asn<br>120 | Pro | Ala | Met | Pro | Thr<br>125 | Ser | Ser | Gly |
| Ser | Glu<br>130 | Gly | Asn | Val | Lys | Leu<br>135 | Cys | Ser | Leu | Glu | Glu<br>140 | Ala | Gln | Arg | Ile |
| Trp<br>145 | Lys | Gln | Lys | Ser | Ala<br>150 | Glu | Ile | Tyr | Pro | Ile<br>155 | Met | Asp | Lys | Ser | Ser<br>160 |
| Arg | Thr | Arg | Leu | Ala<br>165 | Leu | Ile | Ile | Cys | Asn<br>170 | Glu | Glu | Phe | Asp | Ser<br>175 | Ile |
| Pro | Arg | Arg | Thr<br>180 | Gly | Ala | Glu | Val | Asp<br>185 | Ile | Thr | Gly | Met | Thr<br>190 | Met | Leu |
| Leu | Gln | Asn<br>195 | Leu | Gly | Tyr | Ser | Val<br>200 | Asp | Val | Lys | Lys | Asn<br>205 | Leu | Thr | Ala |
| Ser | Asp<br>210 | Met | Thr | Thr | Glu | Leu<br>215 | Glu | Ala | Phe | Ala | His<br>220 | Arg | Pro | Glu | His |
| Lys<br>225 | Thr | Ser | Asp | Ser | Thr<br>230 | Phe | Leu | Val | Phe | Met<br>235 | Ser | His | Gly | Ile | Arg<br>240 |
| Glu | Gly | Ile | Cys | Gly<br>245 | Lys | Lys | His | Ser | Glu<br>250 | Gln | Val | Pro | Asp | Ile<br>255 | Leu |
| Gln | Leu | Asn | Ala<br>260 | Ile | Phe | Asn | Met | Leu<br>265 | Asn | Thr | Lys | Asn | Cys<br>270 | Pro | Ser |
| Leu | Lys | Asp<br>275 | Lys | Pro | Lys | Val | Ile<br>280 | Ile | Ile | Gln | Ala | Cys<br>285 | Arg | Gly | Asp |
| Ser | Pro<br>290 | Gly | Val | Val | Trp | Phe<br>295 | Lys | Asp | Ser | Val | Gly<br>300 | Val | Ser | Gly | Asn |
| Leu<br>305 | Ser | Leu | Pro | Thr | Thr<br>310 | Glu | Glu | Phe | Glu | Asp<br>315 | Asp | Ala | Ile | Lys | Lys<br>320 |
| Ala | His | Ile | Glu | Lys<br>325 | Asp | Phe | Ile | Ala | Phe<br>330 | Cys | Ser | Ser | Thr | Pro<br>335 | Asp |
| Asn | Val | Ser | Trp<br>340 | Arg | His | Pro | Thr | Met<br>345 | Gly | Ser | Val | Phe | Ile<br>350 | Gly | Arg |
| Leu | Ile | Glu<br>355 | His | Met | Gln | Glu | Tyr<br>360 | Ala | Cys | Ser | Cys | Asp<br>365 | Val | Glu | Glu |
| Ile | Phe<br>370 | Arg | Lys | Val | Arg | Phe<br>375 | Ser | Phe | Glu | Gln | Pro<br>380 | Asp | Gly | Arg | Ala |
| Gln<br>385 | Met | Pro | Thr | Thr | Glu<br>390 | Arg | Val | Thr | Leu | Thr<br>395 | Arg | Cys | Phe | Tyr | Leu<br>400 |
| Phe | Pro | Gly | His | | | | | | | | | | | | |

( 2 ) INFORMATION FOR SEQ ID NO:3:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:3:

GGGGAATTCA TGAACCCGGC TATGCCGACC TCTTCTGGTT CTGAAGGTAA CGTTAAACTG    60

TGCTCTCTGG AAGAAGC    77

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:4:

CCCCACTAGT CCTCTATTAA TCTTTAAACC ACACCACACC AGGGC    45

(2) INFORMATION FOR SEQ ID NO:5:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:5:

GGGGAATTCA TGGCTATCAA AAAAGCTCAC ATCGAAAAAG ACTTCATCGC TTTCTGC    57

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:6:

CCCCACTAGT CCTCTATTAA TGTCCTGGGA AGAGG    35